United States Patent
Che et al.

(10) Patent No.: US 8,563,712 B2
(45) Date of Patent: Oct. 22, 2013

(54) HYDROXY-SUBSTITUTED GOLD(III) PORPHYRIN COMPLEXES AS HISTONE DEACETYLASE INHIBITORS

(75) Inventors: Chi Ming Che, Hong Kong (HK); Yu Wang, Hong Kong (HK); Raymond Wai Yin Sun, Honk Kong (HK); Kim Hei-Man Chow, Hong Kong (HK)

(73) Assignee: The University of Hong Kong, Hong Kong (HK)

( * ) Notice: Subject to any disclaimer, the term of this patent is extended or adjusted under 35 U.S.C. 154(b) by 194 days.

(21) Appl. No.: 12/913,398

(22) Filed: Oct. 27, 2010

(65) Prior Publication Data

US 2011/0098263 A1    Apr. 28, 2011

Related U.S. Application Data

(60) Provisional application No. 61/255,668, filed on Oct. 28, 2009.

(51) Int. Cl.
*C07D 487/22* (2006.01)

(52) U.S. Cl.
USPC .......................................... 540/145

(58) Field of Classification Search
USPC .......................................... 540/145
See application file for complete search history.

(56) References Cited

U.S. PATENT DOCUMENTS 6,087,493 A    7/2000  Wheelhouse et al.

OTHER PUBLICATIONS

Stordal, et al. A systematic review of platinum and taxane resistance from bench to clinic: An inverse relationship. Cancer Treatment Reviews, 2007, pp. 688-703.

Shaw. Gold-Based Therapeutic Agents. Chem. Review, 1999, 99, pp. 2589-2600.

Che. et al. Gold (III) Porphyrins as a new class of anticancer drugs: cytotoxicity, DNA binding and induction of apoptosis in human cervix epitheloid cancer cells. Chem. Comm., 2003, pp. 1718-1719.

Sun, et al. The anti-cancer properties of gold (III) compounds with dianionic porphyrin and tetradentate ligands. Coordination Chemistry Reviews, 253, 2009, pp. 1682-1691.

*Primary Examiner* — Brian McDowell
(74) *Attorney, Agent, or Firm* — Turocy & Watson, LLP

(57) ABSTRACT

A method for treatment of cancer by inhibiting the activity of histone deacetylase, comprising administering to a human in need of such treatment a composition containing a therapeutically effective amount of a gold(III) complex having the structural formula of

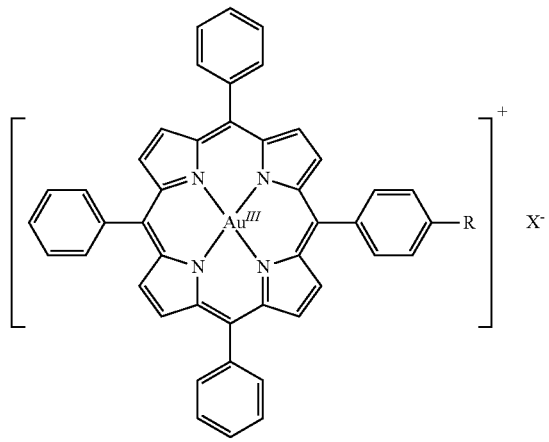

or a pharmaceutically acceptable salt thereof, wherein:
—R is selected from the group consisting of —OH, —CH$_2$OH, C$_2$H$_4$OH, —C$_3$H$_6$OH or —C$_4$H$_8$OH; and
X is independently a pharmaceutically acceptable counterion.

9 Claims, 8 Drawing Sheets

HYDROXY-SUBSTITUTED GOLD(III) PORPHYRIN COMPLEXES AS HISTONE DEACETYLASE INHIBITORS

CROSS-REFERENCE TO RELATED APPLICATIONS

This application claims priority to provisional application Ser. No. 61/255,668, filed on Oct. 28, 2009, which is incorporated herein by reference.

TECHNICAL FIELD

Described herein are gold(III) complexes as histone deacetylase inhibitors, pharmaceutical compositions including same useful, and methods for treatment of cancer using such compositions.

BACKGROUND

Although various chemotherapeutic agents such as cisplatin and its derivatives can effectively cure patients with various types of cancer, the clinical success is compromised by the emergence of drug resistance and toxic side effects [B. Stordal, et al, *Cancer Treat. Rev.* 2007, 33, 688]. Breast cancer represents the most common diagnosed female malignancy and the second leading cause of women death worldwide. Treatments including surgery, radiotherapy, chemotherapy and endocrine therapy are effective at the early stage. For recurrent and metastatic breast carcinoma, available treatment options are limited, and in most cases, chemotherapy remains the only choice. Chemotherapeutic agents, such as cisplatin and its derivatives, doxorubicin, fluorouracil and monoclonal antibody trastuzumab are commonly used and usually given in the form of combinational chemotherapy. However, the effects of these agents are not universal, and a large portion of patients develop resistance. Moreover, side effects including induction of life-threatening toxicity are commonly encountered. Therefore, there is a great urge for the development of new alternative chemotherapeutic agents with fewer side effects.

Therapeutic values of metallic gold and gold salts have been recognized thousands of years ago and its rational use in medicine began in early 1920s. In recent decades, various gold(III) complexes have been reported to exhibit cytotoxicities against a broad spectrum of tumor cells. However, their instabilities in physiological condition have limited their therapeutic usage [C. F. Shaw, *Chem. Rev.* 1999, 99, 2589]. In the design of physiologically stable anti-cancer gold(III) complexes, Che and co-workers have employed strongly chelating porphyrinato ligands to stabilize a gold(III) ion [C.-M. Che, et al, *Chem. Commun.* 2003, 1718; R. W.-Y. Sun, et al, *Coord. Chem. Rev.* 2009, 253, 1682]. These gold(III) porphyrin complexes were found to display promising in vitro and in vivo anti-cancer activities towards a panel of cell lines including hepatocellular carcinoma, nasopharyngeal carcinoma, neuroblastoma and colon cancer. Yet, these complexes are poorly soluble in aqueous solution as hydrophilic substitution groups including (hydroxyl group) are absence in these complexes.

In addition to the gold(III) porphyrin complex, Wheelhouse et al [U.S. Pat. No. 6,087,493; hereafter "Wheelhouse"] has disclosed the use of porphyrin compounds and metalloporphyrin complexes contain pyridyl or quinolyl aldehyde derivatives to inhibit telomerase activity and hence, proliferation of cancer cells. Wheelhouse also disclosed that porphyrins which do not contain pyridyl or quinolyl aldehydes are inactive toward for the telomerase inhibition.

In the present invention, we have focused the use of hydroxy-substituted gold(III) porphyrin complexes as histone deacetylase inhibitors. These complexes are designed to block the active site of histone deacetylase and hence inhibit its activity.

SUMMARY

The following presents a simplified summary of the invention in order to provide a basic understanding of some aspects of the invention. This summary is not an extensive overview of the invention. It is intended to neither identify key or critical elements of the invention nor delineate the scope of the invention. Rather, the sole purpose of this summary is to present some concepts of the invention in a simplified form as a prelude to the more detailed description that is presented hereinafter.

Described herein are methods for the treatment of cancer by inhibiting the activity of histone deacetylase, involving administering to a human in need of such treatment a composition comprising a therapeutically effective amount of a gold(III) complex having the structural formula of

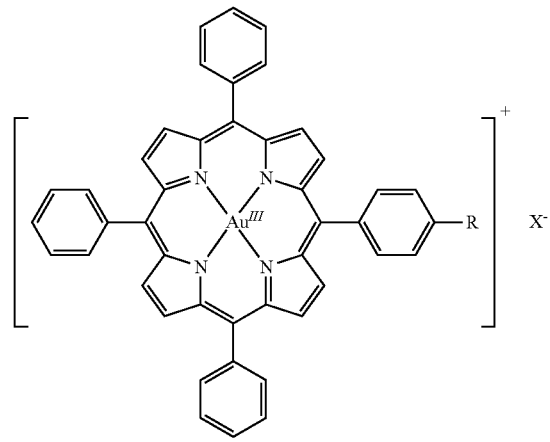

or a pharmaceutically acceptable salt thereof, wherein:
R is selected from the group consisting of —OH, —CH$_2$OH, C$_2$H$_4$OH, —C$_3$H$_6$OH or —C$_4$H$_8$OH;
X is independently a pharmaceutically acceptable counterion.

DETAILED DESCRIPTION

Figure 1:
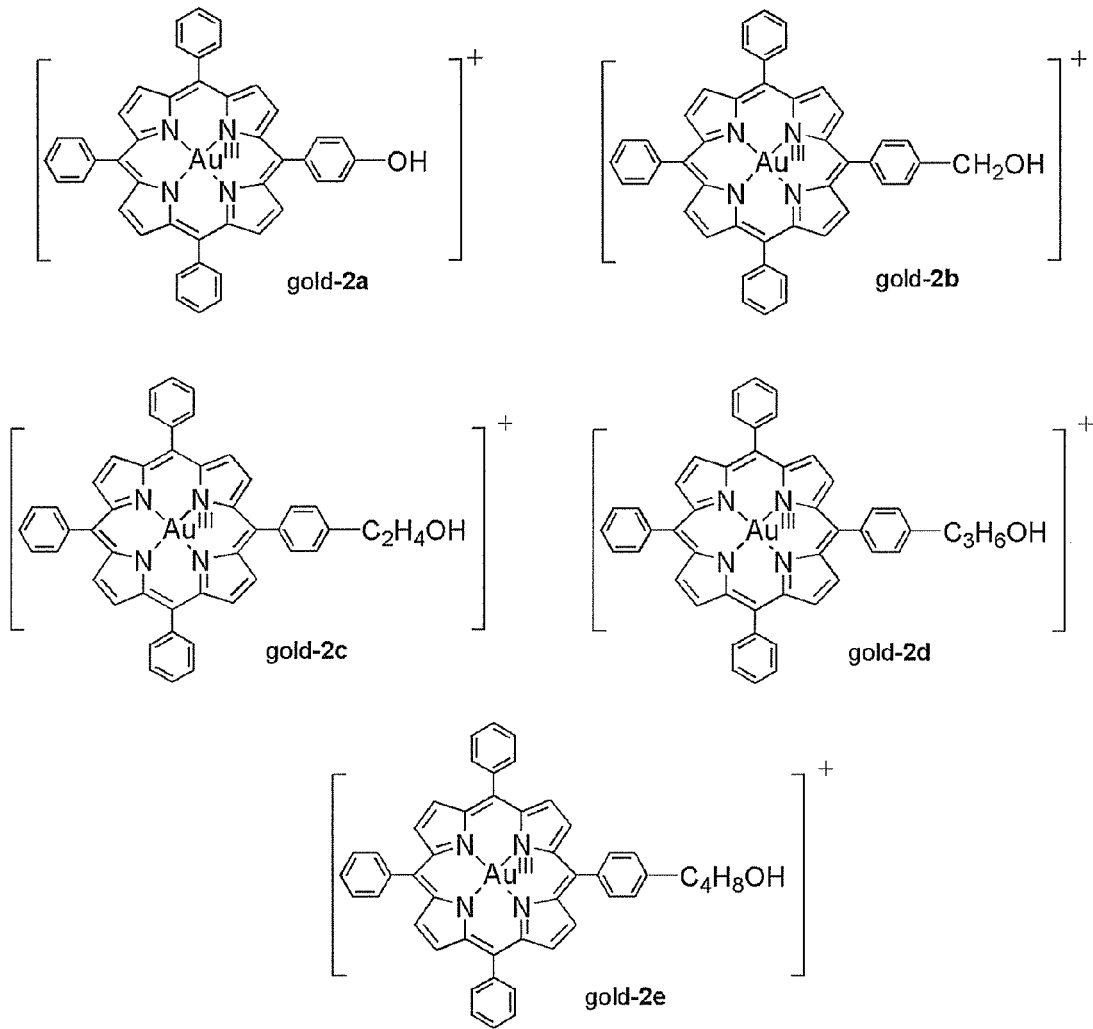
FIG. 1 shows chemical structures of the hydroxy-substituted gold(III) porphyrin complexes gold-2a-gold-2e.

Described herein is the use of hydroxy-substituted gold (III) [or Au(III) or Au$^{III}$] porphyrin complexes useful as anti-tumor agents and to pharmaceutical compositions and the use of the hydroxy-substituted gold(III) porphyrin complexes for combating cancer. The pharmaceutical compositions contain different synthetic hydroxy-substituted gold(III) porphyrin complexes in amounts effective to induce cancer cell death. The hydroxy-substituted gold(III) porphyrin complexes also provides a method of inhibiting the growth of tumor cells in a human afflicted with cancer that involves administering to such human an effective tumor cell growth inhibiting amount of a hydroxy-substituted gold(III) porphyrin complex. Evidence reported herein suggests that the gold(III) compounds exert their anti-proliferative activities through mechanisms that are substantially different from those of platinum drugs such as cisplatin. Specifically, data reported herein indicates that the gold(III) complexes bind and form a complex with histone deacetylase.

Previously, we have reported a series of gold(III) meso-tetraarylporphyrin complexes. Among them, the gold-1a complex ([Au$^{III}$(TPP)]Cl) showed some anti-proliferative activities against a panel of human cancer cells including those derived from nasopharyngeal and hepatocellular carcinoma. Here, we report novel gold(III) porphyrins with hydroxyl substitution (gold-2a through gold-2e shown in FIG. 1). These novel compounds show a surprising improvement in aqueous solubility and stability. Further, the efficacy of gold-2a was unexpectedly effective in suppressing in vitro and in vivo growth of human breast cancer cells. In contrast, the previous gold-1a complex showed no inhibition of breast tumor growth at sub-lethal concentrations.

Regarding the anti-cancer mechanism, convincing evidence shown herein indicates that the introduction of a hydroxy substitution group imparts the ability in gold-2a to selectively inhibit Wnt/β-catenin signaling through modulating histone deacetylase activities. As shown by computational experiment, gold-2a shows higher binding affinity to the histone deacetylase compared to the unsubstituted gold-1a. Notably, gold-2a does not display any activity on telomerase inhibition, which the telomerase has been reported to be the target of a series of porphyrin and metalloporphyrin complexes [U.S. Pat. No. 6,087,493; hereafter "Wheelhouse"]. Therefore, the gold(III) complexes reported here operate through an unexpected molecular mechanism to achieve a very high degree of anti-tumor efficacy.

It will be understood that, in one embodiment, the hydroxy-substituted porphyrin molecule and the gold(III) center do not form a neutral complex. For instance, the net positive charge on the gold(III) can be greater than the absolute net negative charge of the hydroxy-substituted porphyrin molecule. In these embodiments, there can be a counter-anion coordinated to the gold(III) complex for charge neutralization. Accordingly, the phrase "pharmaceutically acceptable salt," as used herein, includes salts formed from a charged gold(III) complex and counter anion.

As used herein, the term "histone deacetylase(s)" are a class of enzymes that remove acetyl groups from an ε-N-acetyl lysine amino acid on a histone. Histone deacetylase proteins are also referred to as lysine deacetylases, as to more precisely describe the function rather than the target.

As used herein, the term "hydroxy-substituted porphyrin molecule" refers to a molecule of the following chemical structure:

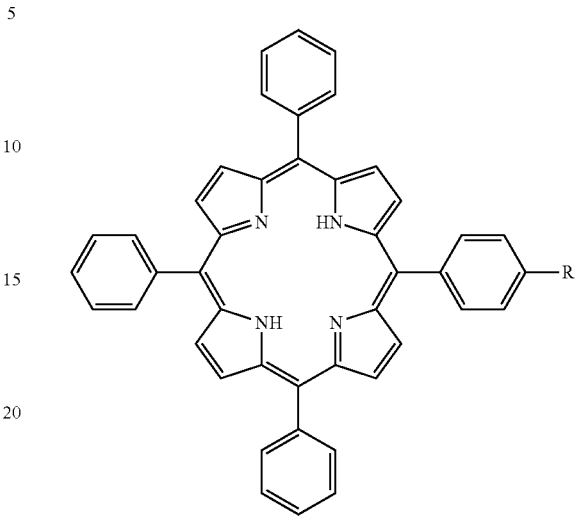

wherein,
R is selected from the group consisting of —OH, —CH$_2$OH, C$_2$H$_4$OH, —C$_3$H$_6$OH or —C$_4$H$_8$OH. That is, R is a hydroxyl containing group including alkoxy groups having from 1 to 5 carbon atoms. In another embodiment, R is a hydroxyl containing group including hydroxyl and alkoxy groups having from 1 to 4 carbon atoms.

As used herein, the phrase "counter-anion" refers to an ion associated with a positively charged gold(III) complex. Non-limiting examples of counter-anions include halogens such as fluoride, chloride, bromide, and iodide, sulfate, phosphate, trifluoromethanesulfonate, acetate, nitrate, perchlorate, acetylacetonate, hexafluoroacetylacetonate and hexafluorophosphate.

As used herein, the term "hydroxy-substituted gold(III) porphyrin complexes" refers to complex of gold(III) metal bound to any hydroxy-substituted porphyrin molecule. The structure of the hydroxy-substituted gold(III) porphyrin complexes can exist as a single molecule or aggregated molecules.

As used herein, the phrase of "pharmaceutically acceptable carrier" means a carrier combination of carrier ingredients approved by a regulatory agency of the Federal or a state government or listed in the U.S. Pharmacopoeia or other generally recognized pharmacopoeia for use in animals, mammals, and more particularly in humans. Non-limiting examples of pharmaceutically acceptable carriers include liquids, such as water and oils, including those of petroleum, animal, vegetable, or synthetic origin. Water is a frequently used vehicle when the compound of the invention is administered intravenously. Saline solutions and aqueous dextrose and glycerol solutions can also be employed as liquid vehicles, particularly for injectable solutions.

As noted above, the present invention relates to compositions useful for the induction of cancer cell death.

As noted above, the term "cancer" refers but not limited to breast carcinoma, cervical epithelioid carcinoma, hepatocellular carcinoma, leukemia, nasopharyngeal carcinoma, melanoma and lung carcinoma.

In one embodiment, the invention relates to a method for induction of cancer cell death (including but not limited to apoptosis) of cancer cells comprising administering to a patient afflicted with a responsive form of cancer a composition comprising an effective amount of one or more hydroxy-substituted gold(III) porphyrin complexes. The hydroxy-substituted gold(III) porphyrin complexes can be represented by the following structural formula, or a pharmaceutically acceptable salt thereof:

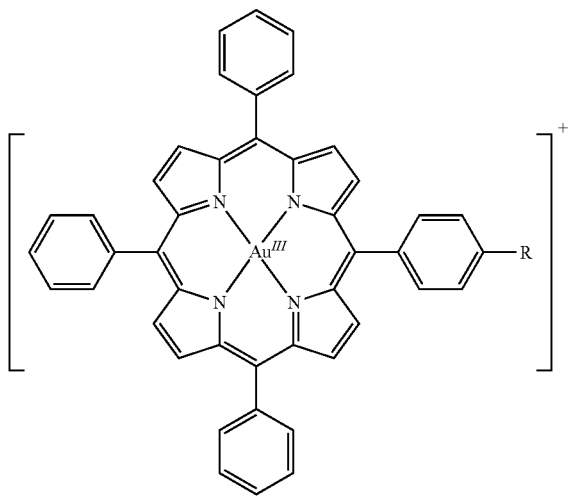

wherein R is as described above.

In another embodiment, the invention relates to a method for the induction of cancer cell death comprising administering to a patient in need thereof a composition comprising an effective amount of a hydroxy-substituted gold(III) porphyrin complex or a pharmaceutically acceptable salt thereof, wherein R is OH (gold-2a).

In another embodiment, the invention relates to a method for the induction of cancer cell death comprising administering to a patient in need thereof a composition comprising an effective amount of a hydroxy-substituted gold(III) porphyrin complex or a pharmaceutically acceptable salt thereof, wherein R is $CH_2OH$ (gold-2b).

In another embodiment, the invention relates to a method for the induction of cancer cell death comprising administering to a patient in need thereof a composition comprising an effective amount of a hydroxy-substituted gold(III) porphyrin complex or a pharmaceutically acceptable salt thereof, wherein R is $C_2H_4OH$ (gold-2c).

In another embodiment, the invention relates to a method for the induction of cancer cell death comprising administering to a patient in need thereof a composition comprising an effective amount of a hydroxy-substituted gold(III) porphyrin complex or a pharmaceutically acceptable salt thereof, wherein R is $C_3H_6OH$ (gold-2d).

In another embodiment, the invention relates to a method for the induction of cancer cell death comprising administering to a patient in need thereof a composition comprising an effective amount of a hydroxy-substituted gold(III) porphyrin complex or a pharmaceutically acceptable salt thereof, wherein R is $C_4H_8OH$ (gold-2e).

FIG. 1 shows illustrative examples of the hydroxy-substituted gold(III) porphyrin complexes useful in the present invention.

Generally, the hydroxy-substituted gold(III) porphyrin complexes are made by reacting under suitable conditions a gold compound with a hydroxylphenyl-triphenylporphyrin compound. Examples of gold compounds include potassium chloroaurate, sodium chloroaurate, and the like. Examples of hydroxylphenyl-triphenylporphyrin compounds include 5-hydroxyphenyl-10,15,20-triphenylporphyrin, 5-(hydroxymethyl)phenyl-10,15,20-triphenylporphyrin, 5-(hydroxyethyl)phenyl-10,15,20-triphenylporphyrin, 5-(n-hydroxypropyl)phenyl-10,15,20-triphenylporphyrin, 5-(n-hydroxybutyl)phenyl-10,15,20-triphenylporphyrin, and the like. In one embodiment, the reaction is conducted under elevated temperatures, such as from 30° C. to 100° C. under acidic conditions. In another embodiment, the reaction is conducted under elevated temperatures from 50° C. to 90° C.

EXAMPLES

Example 1

Preparation and Characterization of the Gold(III) Complexes

In general, the syntheses of hydroxy-substituted gold(III) porphyrin complexes (FIG. 1) were conducted under a nitrogen atmosphere using the standard Schlenk technique [C.-M. Che, et al, *Chem. Commun.* 2003, 1718], which is incorporated herein by reference. For the synthesis of gold-2a, K[AuCl$_4$] (0.508 mmol) and sodium acetate (2.538 mmol) were heated to 80° C. in acetic acid (20 mL) for 15 minutes. A solution of 5-hydroxyphenyl-10,15,20-triphenylporphyrin (0.406 mmol) in acetic acid (10 mL) was added dropwise. The mixture was heated under reflux for 2 h. Upon removal of solvent by vacuum, the residue was dissolved in CH$_2$Cl$_2$ (40 mL). The CH$_2$Cl$_2$ solution was washed twice with water (2×40 mL) to remove any unreacted KAuCl$_4$ and sodium acetate, and concentrated to approximately 3 mL. It was chromatographed on a neutral 90-alumina packed column with CH$_2$Cl$_2$ as eluent to remove the unreacted 5-hydroxyphenyl-10,15,20-triphenylporphyrin, and the gold(III) complex was then eluted using a CH$_2$Cl$_2$/MeOH (99:1, v/v) mixture. A reddish-purple solid was obtained after solvent evaporation and the complex was recrystallized from a CH$_2$Cl$_2$/diethylether (1:1, v/v) mixture. $^1$H NMR spectrum was recorded on a DPX-400 Bruker FT-NMR spectrometer with chemical shift (in ppm) relative to tetramethylsilane. Absorption spectrum was recorded on a Perkin-Elmer Lambda 900 UV-vis spectrophotometer. Mass spectrum (FAB) was recorded on a Finnigan MAT95 mass spectrometer using 3-nitrobenzyl alcohol (NBA) as matrix. Elemental analysis was performed by the Institute of Chemistry at Chinese Academy of Sciences, Beijing. The gold-2a was obtained at a yield of 77%. $^1$H NMR (CDCl$_3$): δ=9.44 (d, J=5.2 Hz, 2H), 9.30-9.25 (m, 6H), 8.23 (d, J=6.3 Hz, 6H), 7.93-7.79 (m, 11H), 7.32 (d, J=8.4 Hz, 2H). UV-vis (DMSO) $\lambda_{max}$/nm (log ε): 414 (5.35), 526 (4.30). FAB-MS: m/z 826 [M$^+$]; elemental analysis calcd (%) for C$_{44}$H$_{28}$N$_4$OClAu: C, 61.37; H, 3.28; N, 6.51. Found: C, 61.54; H, 3.17; N, 6.46

For the synthesis of gold-2b, K[AuCl$_4$] (0.508 mmol) and sodium acetate (2.538 mmol) were heated to 80° C. in acetic acid (20 mL) for 15 minutes. A solution of 5-(hydroxymethyl)phenyl-10,15,20-triphenylporphyrin (0.406 mmol) in acetic acid (10 mL) was added dropwise. The mixture was heated under reflux for 2 h. Upon removal of solvent by vacuum, the residue was dissolved in CH$_2$Cl$_2$ (40 mL). The CH$_2$Cl$_2$ solution was washed twice with water (2×40 mL) to remove any unreacted KAuCl$_4$ and sodium acetate, and concentrated to approximately 3 mL. It was chromatographed on a neutral 90-alumina packed column with CH$_2$Cl$_2$ as eluent to remove the unreacted porphyrin, and the gold(III) complex was then eluted using a CH$_2$Cl$_2$/MeOH (99:1, v/v) mixture. A reddish-purple solid was obtained after solvent evaporation and the complex was recrystallized from a $CH_2Cl_2$/diethylether (1:1, v/v) mixture.

For the synthesis of gold-2c, $K[AuCl_4]$ (0.508 mmol) and sodium acetate (2.538 mmol) were heated to 80° C. in acetic acid (20 mL) for 15 minutes. A solution of 5-(hydroxyethyl)phenyl-10,15,20-triphenylporphyrin (0.406 mmol) in acetic acid (10 mL) was added dropwise. The mixture was heated under reflux for 2 h. Upon removal of solvent by vacuum, the residue was dissolved in $CH_2Cl_2$ (40 mL). The $CH_2Cl_2$ solution was washed twice with water (2×40 mL) to remove any unreacted $KAuCl_4$ and sodium acetate, and concentrated to approximately 3 mL. It was chromatographed on a neutral 90-alumina packed column with $CH_2Cl_2$ as eluent to remove the unreacted porphyrin, and the gold(III) complex was then eluted using a $CH_2Cl_2$/MeOH (99:1, v/v) mixture. A reddish-purple solid was obtained after solvent evaporation and the complex was recrystallized from a $CH_2Cl_2$/diethylether (1:1, v/v) mixture.

For the synthesis of gold-2d, $K[AuCl_4]$ (0.508 mmol) and sodium acetate (2.538 mmol) were heated to 80° C. in acetic acid (20 mL) for 15 minutes. A solution of 5-(n-hydroxypropyl)phenyl-10,15,20-triphenylporphyrin (0.406 mmol) in acetic acid (10 mL) was added dropwise. The mixture was heated under reflux for 2 h. Upon removal of solvent by vacuum, the residue was dissolved in $CH_2Cl_2$ (40 mL). The $CH_2Cl_2$ solution was washed twice with water (2×40 mL) to remove any unreacted $KAuCl_4$ and sodium acetate, and concentrated to approximately 3 mL. It was chromatographed on a neutral 90-alumina packed column with $CH_2Cl_2$ as eluent to remove the unreacted porphyrin, and the gold(III) complex was then eluted using a $CH_2Cl_2$/MeOH (99:1, v/v) mixture. A reddish-purple solid was obtained after solvent evaporation and the complex was recrystallized from a $CH_2Cl_2$/diethylether (1:1, v/v) mixture.

For the synthesis of gold-2e, $K[AuCl_4]$ (0.508 mmol) and sodium acetate (2.538 mmol) were heated to 80° C. in acetic acid (20 mL) for 15 minutes. A solution of 5-(n-hydroxybutyl)phenyl-10,15,20-triphenylporphyrin (0.406 mmol) in acetic acid (10 mL) was added dropwise. The mixture was heated under reflux for 2 h. Upon removal of solvent by vacuum, the residue was dissolved in $CH_2Cl_2$ (40 mL). The $CH_2Cl_2$ solution was washed twice with water (2×40 mL) to remove any unreacted $KAuCl_4$ and sodium acetate, and concentrated to approximately 3 mL. It was chromatographed on a neutral 90-alumina packed column with $CH_2Cl_2$ as eluent to remove the unreacted porphyrin, and the gold(III) complex was then eluted using a $CH_2Cl_2$/MeOH (99:1, v/v) mixture. A reddish-purple solid was obtained after solvent evaporation and the complex was recrystallized from a $CH_2Cl_2$/diethylether (1:1, v/v) mixture.

Example 2

Gold(III) Complexes Exert Potent Anti-Proliferative Activities Against Human Cancer Cells Five types of human breast carcinoma cells with distinct gene expression profiles and oncogenic phenotypes, including BT474, MCF-7, T47D, MDA-MB-231 and SKBR3, which is incorporated herein by reference, were used for evaluating the cytotoxicity of gold-2a. Crystal violet assay demonstrated that gold-2a inhibited growth of all five types of cells with mean $IC_{50}$ values of 0.49±0.17 µM, 0.08±0.04 µM, 0.04±0.01 µM, 0.007±0.002 µM, and 0.02±0.01 µM, respectively (0.5% FBS condition, 24 h treatment; Table 1). The presence of high concentrations of serum had no effects on the potencies of the drug. In contrast, the $IC_{50}$ values of cisplatin were ~100-3000 times higher when compared to gold-2a. Similar results were observed when the drug exposure time was extended to 48 h. It should be noted that the $IC_{50}$ values of gold-2a were one to two log lower in MDA-MB-231 cells than the other four types of cells under all conditions. On the other hand, the potency of gold-2a towards noncancerous fibroblast cell was ~10-600 folds lower than those of mammary cancer cells, with an $IC_{50}$ of 4.17±1.67 µM. The antiproliferative activity of another gold(III) porphyrin complex ($[Au^{III}(TPP)]Cl$, gold-1a) in MDA-MB-231 cells was also tested. Non-linear regression analysis of the growth inhibition curves revealed that gold-1a was ~1000 fold less effective than gold-2a. Apoptosis of MDA-MB-231 cells were evaluated by measuring DNA fragmentation. The results showed that gold-2a significantly increased DNA fragmentation in a dose- and time-dependent manner (FIG. 2A). TUNEL analysis confirmed that the number of apoptotic cells was augmented by gold-2a treatments (FIG. 2B).

Figure 2:
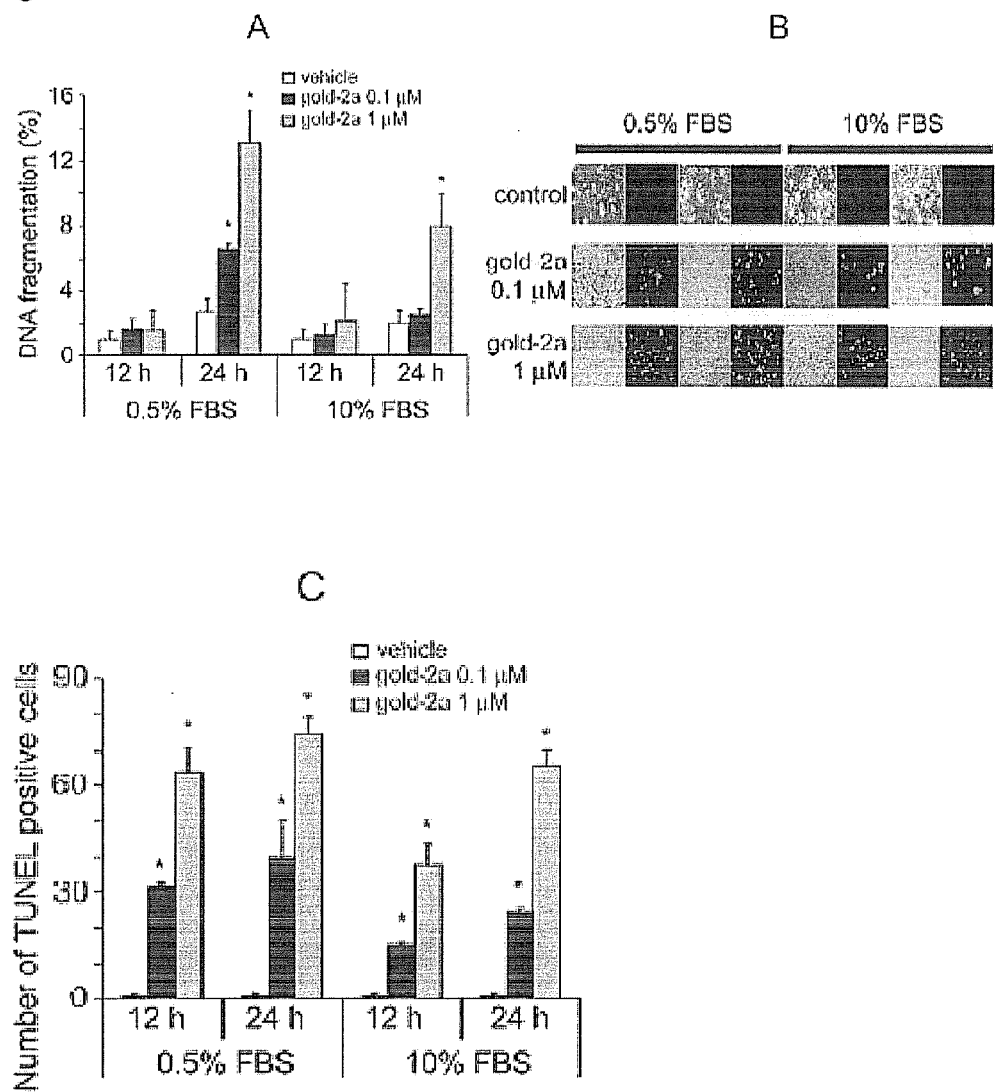
FIG. 2 shows the induced apoptotic properties of gold-2a in MDA-MB-231 cells.

FIG. 2 shows the induced apoptotic properties of gold-2a in MDA-MB-231 cells. A, MDA-MB-231 cells were labeled with [$^3$H]-thymidine and incubated with gold-2a (0.1 µM or 1 µM) for different periods. Fragmented DNA was measured as described in Methods. B, MDA-MB-231 cells treated with or without gold-2a were subjected to TUNEL for evaluating the number of apoptotic cells. Both phase contrast and fluorescence representative images were shown. C, The number of TUNEL positive cells was counted in eight random areas and averaged for each sample. *, $P<0.05$ vs vehicle control, n=5.

The antiproliferative activity tests of gold-2b, gold-2c, gold-2d and gold-2e were conducted by the same test described for gold-2a. The $IC_{50}$ values of gold-2b, gold-2c, gold-2d and gold-2e towards MDA-MB-231 cells were found to be 0.2±0.02 µM, 0.16±0.03 µM, 0.03±0.01 µM and 0.02±0.01 µM, respectively.

In addition to breast carcinoma, the cytotoxicity of gold-2a towards human cervical epithelioid carcinoma (HeLa), hepatocellular carcinoma (HepG2), leukemia (HL-60), nasopharyngeal (SUNE1), melanoma (B16) and lung carcinoma has been determined; corresponding $IC_{50}$ values was found to be 0.08±0.01 µM, 0.21±0.03 µM, 0.11±0.02 µM, 0.31±0.09 µM and 0.22±0.05 µM.

TABLE 1

Anti-proliferative activities of gold-2a and cisplatin in various human breast carcinoma cells.

| Drug | Period of treatment (hours) | Condition | $IC_{50}$ (µM) | | | | |
|---|---|---|---|---|---|---|---|
| | | | BT474 | MCF7 | MDA-MB-231 | SKBR3 | T47D |
| Gold-2a | 24 | 0.5% FBS | 0.49 ± 0.17 | 0.08 ± 0.04 | 0.007 ± 0.002 | 0.02 ± 0.01 | 0.04 ± 0.01 |
| | | 10% FBS | 0.39 ± 0.18 | 0.16 ± 0.08 | 0.003 ± 0.008 | 0.04 ± 0.02 | 0.06 ± 0.03 |

TABLE 1-continued

Anti-proliferative activities of gold-2a and cisplatin in various human breast carcinoma cells.

| Drug | Period of treatment (hours) | Condition | IC$_{50}$ (µM) | | | | |
|------|------|------|------|------|------|------|------|
| | | | BT474 | MCF7 | MDA-MB-231 | SKBR3 | T47D |
| Cisplatin | 48 | 0.5% FBS | 0.15 ± 0.07 | 0.07 ± 0.04 | 0.004 ± 0.001 | 0.07 ± 0.002 | 0.02 ± 0.01 |
| | | 10% FBS | 0.12 ± 0.09 | 0.05 ± 0.01 | 0.001 ± 0.006 | 0.08 ± 0.01 | 0.05 ± 0.01 |
| | 24 | 0.5% FBS | 49.0 ± 0.50 | 14.3 ± 1.46 | 7.37 ± 1.19 | 65.9 ± 25.5 | 66.5 ± 12.4 |
| | | 10% FBS | 45.1 ± 8.20 | 20.1 ± 4.92 | 21.0 ± 11.2 | 76.3 ± 33.8 | 99.4 ± 5.71 |
| | 48 | 0.5% FBS | 1.60 ± 0.53 | 10.1 ± 1.47 | 6.52 ± 0.48 | 33.9 ± 11.0 | 7.76 ± 5.54 |
| | | 10% FBS | 2.89 ± 0.90 | 15.9 ± 2.33 | 18.4 ± 3.42 | 41.0 ± 7.91 | 6.69 ± 3.14 |

Example 3

Intraductal Delivery of Gold-2a Effectively Attenuates Mammary MDA-MB-231 Tumor Growth in Nude Mice To evaluate the in vivo anti-tumor effects of gold-2a, MDA-MB-231 cells were implanted into athymic nude mice, and different drug dosages tested for the treatment. Bi-weekly intra-peritoneal administration of gold-2a (1.5, 3.0 and 6.0 mg/kg) for up to five weeks dose-dependently attenuated the tumor growth. However, no complete tumor suppression could be achieved despite the animals tolerated the treatment well. Instead, the administration of two bolus of the gold-2a (15 mg/kg) by intraductal injection into tumor xenograft resulted in a complete tumor remission in 50% of the animals at 2 weeks after initial implantation (FIG. 3A). Most of the animals remained in a tumor-free status until day 25, at which recurrence of a tumor was observed. Comparing to gold-2a, intraductal delivery of same dosage of cisplatin attenuated the rates of tumor growth to a much lesser degree. Of note is that ~40% of animals died in the cisplatin treatment group after two injections, whereas those of the PET control and gold-2a treatment groups remained alive during the experimental periods (FIG. 3B). The body weights of both gold-2a and cisplatin treated mice were slightly lower than the PET control group (FIG. 3C). The average tumor weights in gold-2a and cisplatin groups were 0.17 g and 0.42 g, respectively, which were decreased by 73% and 34% when compared to control group (FIG. 3D).

Figure 3:
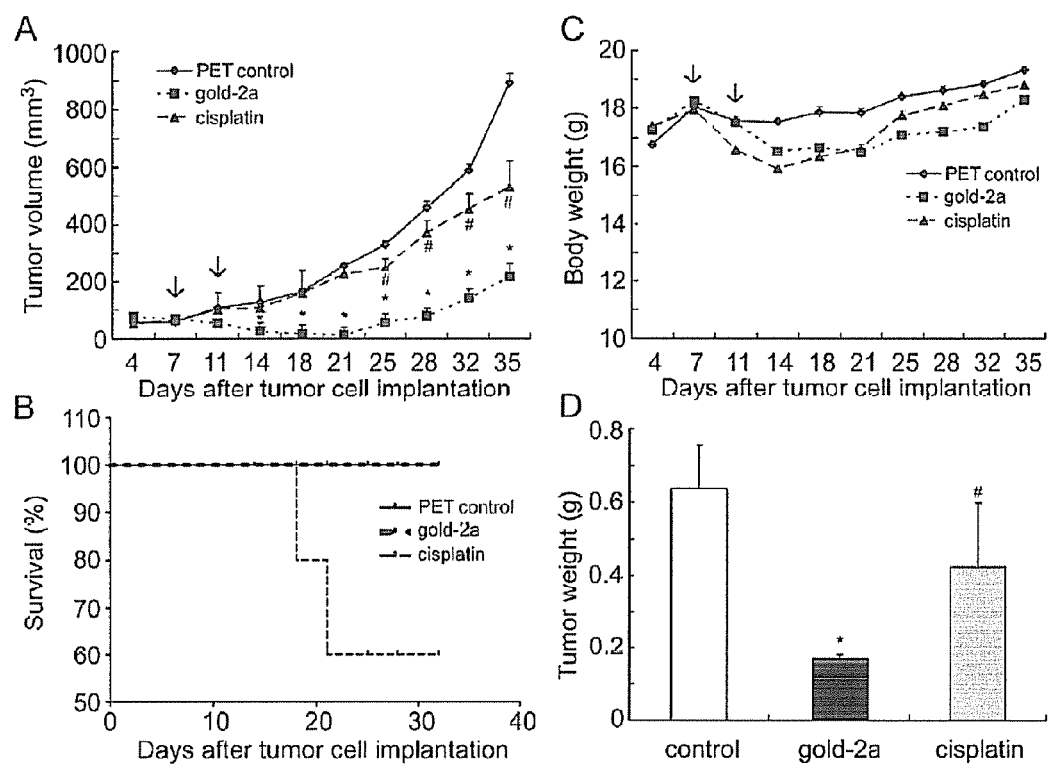
FIG. 3 shows the inhibitory property of gold-2a on tumor growth in nude mice.

FIG. 3 shows the inhibitory property of gold-2a on tumor growth in nude mice. MDA-MB-231 cells were inoculated into the mammary fat pad of nude mice as described in Methods. Gold-2a, cisplatin or PET control was locally injected into the tumor site at Day 7 and Day 11. Tumor growth (A) and body weight (B) were monitored bi-weekly. C, Kaplan-Meier estimates of the survival curves were calculated and plotted. D, At the end of experiment, tumors were collected and weighed. # and *, P<0.05 versus PET control, n=4-6.

Example 4

Gold-2a Inactivates Wnt/β-Catenin Signalling in MDA-MB-231 Cells Through Transcriptional Regulation Aberrant activation of the Wnt/β-catenin signalling plays a key role in the development of many human cancer diseases. Intracellular accumulation of β-catenin protein has been observed in a large portion of human breast tumors. Gold-2a decreased the protein levels of β-catenin in MDA-MB-231 cells as early as four hours after the treatment, under both 0.5% and 10% FBS culture conditions. Nuclear transcriptional activities of β-catenin were also dramatically reduced by gold-2a. On the contrary, cisplatin had no influence on both the protein levels and nuclear activities of β-catenin. In the absence of a Wnt signal, β-catenin is phosphorylated by glycogen synthase kinase-3beta, which facilitates the subsequent ubiquitination and proteasome degradation. However, gold-2a treatment did not alter the relative phosphorylation or ubiquitination levels of β-catenin and had no obvious effects on proteasome activities. Moreover, decreased phosphorylations of Akt and GSK-3β were observed from six hour onwards after gold-2a treatment, later than the effects on β-catenin protein levels. To address the cytotoxic mechanisms and the primary targets of gold-2a, ICP-MS was performed for monitoring the intracellular localization of this complex. The results demonstrated that gold-2a rapidly (within 30 min) entered the nuclei of MDA-MB231 cells and was enriched in the nucleoid fractions.

Figure 4:
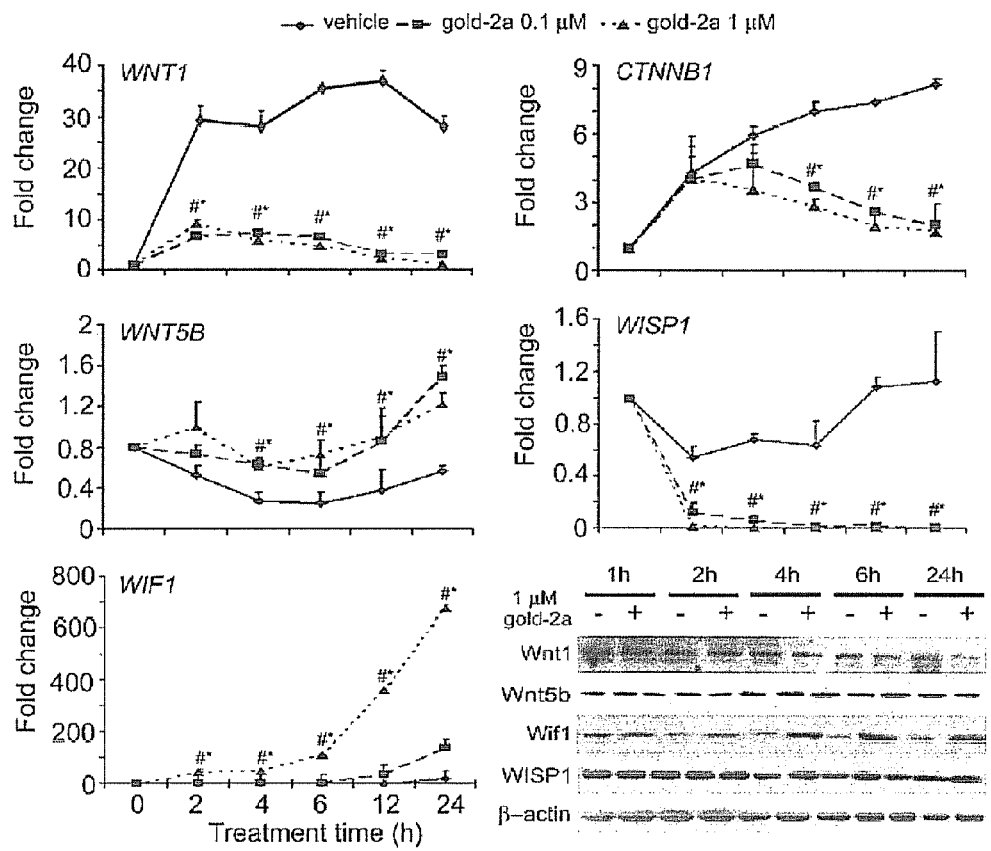
FIG. 4 shows that gold-2a treatment differentially regulates the expression of signaling molecules in Wnt pathway.

The drop in intracellular levels of β-catenin can be triggered by a loss of Wnt signal-induced stabilization. In fact, our quantitative PCR analysis revealed that gold-2a treatment time- and dose-dependently altered the mRNA expressions of several Wnt signalling molecules, including WNT1, WNT5B, WIF1, WISP1 and CTNNB1 (FIG. 4). For instance, gold-2a treatment largely blocked the expression of WNT1, but profoundly augmented the mRNA levels of WIF1. Significant up-regulation of WIF1 (over 80 folds) was observed at as early as two hours, and the stimulatory effects continued during the 24-hour course of treatment. The mRNA levels of WISP1 were rapidly decreased to an undetectable level following gold-2a treatment. The significant effects of gold-2a on CTNNB1 and WNT5B expression were observed from six hours of treatment onwards. Similar trends of changes were also shown for the protein expressions of WNT1, WNT5B, WIF1 and WISP1 (FIG. 4). These results indicated that gold-2a might elicit its anti-proliferative effects through regulating the gene transcriptions of Wnt/β-catenin signalling molecules.

FIG. 4 shows that gold-2a treatment differentially regulates the expression of signaling molecules in Wnt pathway. After 24 hours of serum starvation, MDA-MB-231 cells were treated with gold-2a at 0.1 or 1 µM in normal culture media. At different time points, cells were harvested for quantitative RT-PCR analysis. The relative mRNA abundance of WNT1, WISP1, WNT5B, WIF1 and CTNNB1 were normalized against 18S rRNA and calculated as fold changes comparing to the untreated cells. # and *, P<0.05 for gold-2a treatment at 0.1 µM and 1 µM, respectively, versus vehicle control, n=3. Western blotting was also performed for evaluating the relative protein abundance of the same set of genes with specific antibodies. β-actin was used as the loading control.

Example 5

Figure 5:
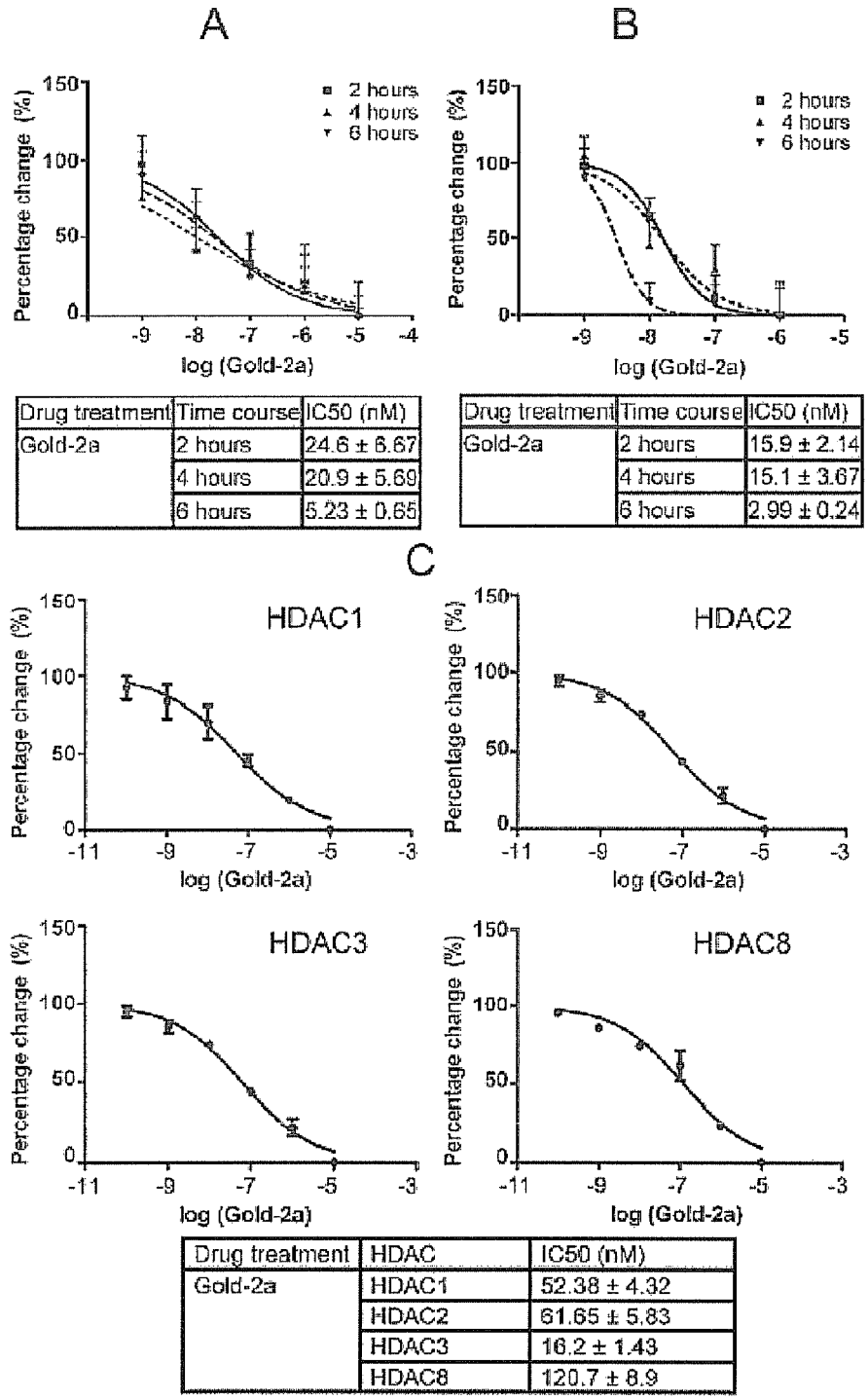
FIG. 5 shows that gold-2a inhibits class I histone deacetylase activities.

Gold-2a Acts as a Selective HDAC Inhibitor to Regulate Histone Acetylation at the Promoter Regions of Genes Involved in Wnt/β-Catenin Signalling The above results demonstrated that gold-2a could selectively enhance the gene expression of WIF1 and non-canonical WNT5B, but inhibit those of WNT1, CTNNB1 and WISP1. Epigenetic regulations, such as DNA methylation and histone acetylation, represent important mechanisms for the aberrant activation of Wnt signalling during cancer development. For example, WIF1 can be silenced by promoter methylation. However, both methylation specific PCR and bisulphite sequencing revealed that the methylation of the proximal region of WIF1 promoter was not altered by gold-2a treatment. On the other hand, the results in FIG. 5 demonstrated that gold-2a exhibited potent inhibitory effects on the enzyme activities of HDAC (histone deacetylase), the dynamic transcriptional regulator for deacetylating chromatin histones. In vivo treatment with gold-2a resulted in a rapid decrease of the HDAC activities in MDA-MB-231 cells (FIG. 5A). The inhibitory effects could also be observed by co-incubation of gold-2a with the nuclear extracts derived from untreated MDA-MB-231 cells (FIG. 5B). Furthermore, the HDAC inhibition was proportional to the incubation time, and the potency of gold-2a was comparable to that of trichostatin A (TSA), a specific inhibitor of multiple HDACs. To test whether gold-2a may act as a preferential inhibitor for certain types of HDAC, individual HDAC (HDAC1 to HDAC9) was immunoprecipitated from the MDA-MB-231 cells and incubated with gold-2a. It should be noted that this complex was able to inhibit the activity of all class I HDACs, including HDAC1, 2, 3 and 8 (FIG. 5C), but not others.

FIG. 5 shows that gold-2a inhibits class I histone deacetylase activities. A, MDA-MB-231 cells were treated with different dosages of gold-2a for two, four and six hours. Nuclear lysates were harvested and HDAC activities measured as described in Methods. $IC_{50}$ was calculated and listed in the Table. B, Nuclear lysates of MDA-MB-231 cells were incubated with gold-2a for different time points and HDAC activity measured as above. $IC_{50}$ was calculated and listed in the Table. C, The immunoprecipitated complexes of HDAC1, 2, 3 and 4 were incubated with different concentrations of gold-2a for one hour and the HDAC activities measured at the end of treatment. n=4, results were from three independent assays.

Figure 6:
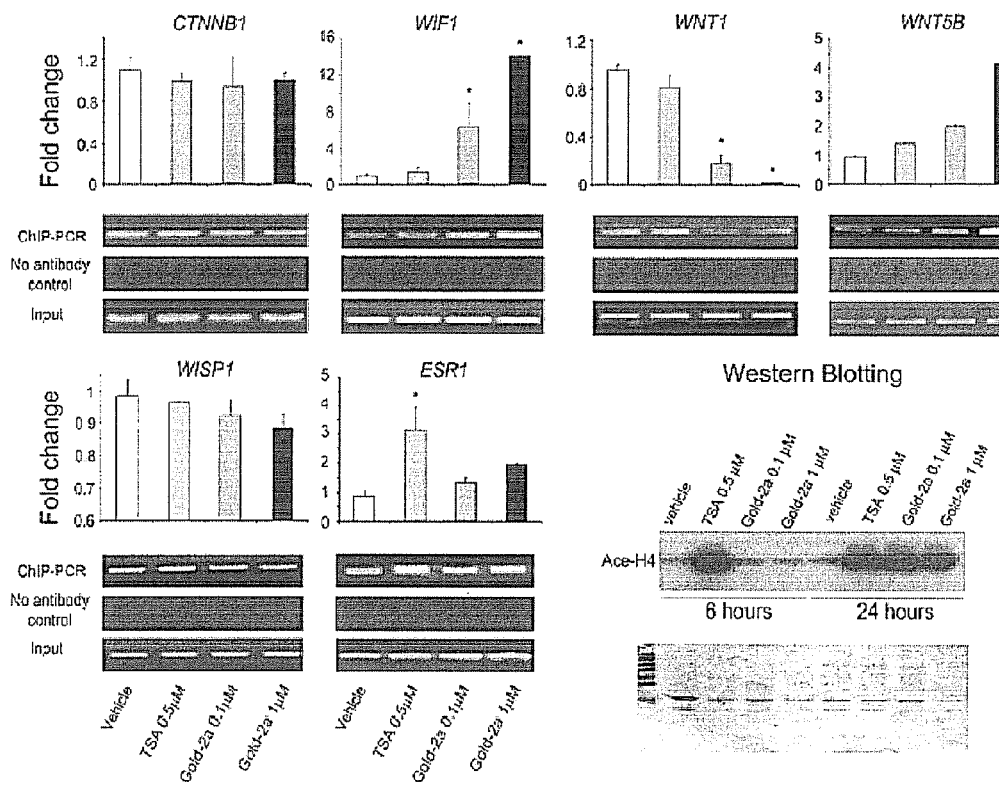
FIG. 6 shows that gold-2a modulates the acetylation status of histone H4 at the promoter regions of Wnt signaling molecules.

To further confirm these unexpected observations, ChIP-PCR was performed to quantify the acetylated histone H4 levels at the promoter regions of the above genes. As the results shown in FIG. 6, treatment with gold-2a enhanced the binding of acetylated histone H4 to WIF1 and WNT5B promoters. In contrast, a decrease in acetylated histone H4 was observed at WNT1 promoter after gold-2a treatment. By contrast, TSA had no significant effects on these three genes, but increased acetylated histone H4 binding to the promoter of estrogen receptor alpha (ESR1). The acetylated histone H4 binding to the promoter of β-catenin gene (CTNNB1) and WISP1 was not significantly altered by gold-2a or TSA treatment. Western blotting analysis showed significant induction of histone H4 acetylation by TSA, which occurred as early as six hours after treatment (FIG. 6). Gold-2a was less effective on global histone H4 acetylation. Similar levels of acetylated histone H4 were only observed at 24 hours after treatment.

FIG. 6 shows that gold-2a modulates the acetylation status of histone H4 at the promoter regions of Wnt signaling molecules. MDA-MB-231 cells were treated with different drugs for 24 hours. ChIP-PCR was performed for analyzing the levels of acetylated histone H4 at the promoter regions of CTNNB1, WIF1, WNT5B, WNT1, WISP1 and ESR1, using antibody recognizing histone H4 acetylated at lysines 5, 8, 12, and 16. Bar charts represented the quantitative results by real time PCR analysis after normalization against the input DNA. Representative agarose gel images were shown at the bottom. Western blotting was performed for analyzing the global acetylated histone H4 (Ace-H4) levels in MDA-MB-231 cells treated with TSA or gold-2a for six and 24 hours respectively. Equal protein loading was confirmed by Amido black staining. *, P<0.01 versus vehicle control, n=3.

Figure 7:
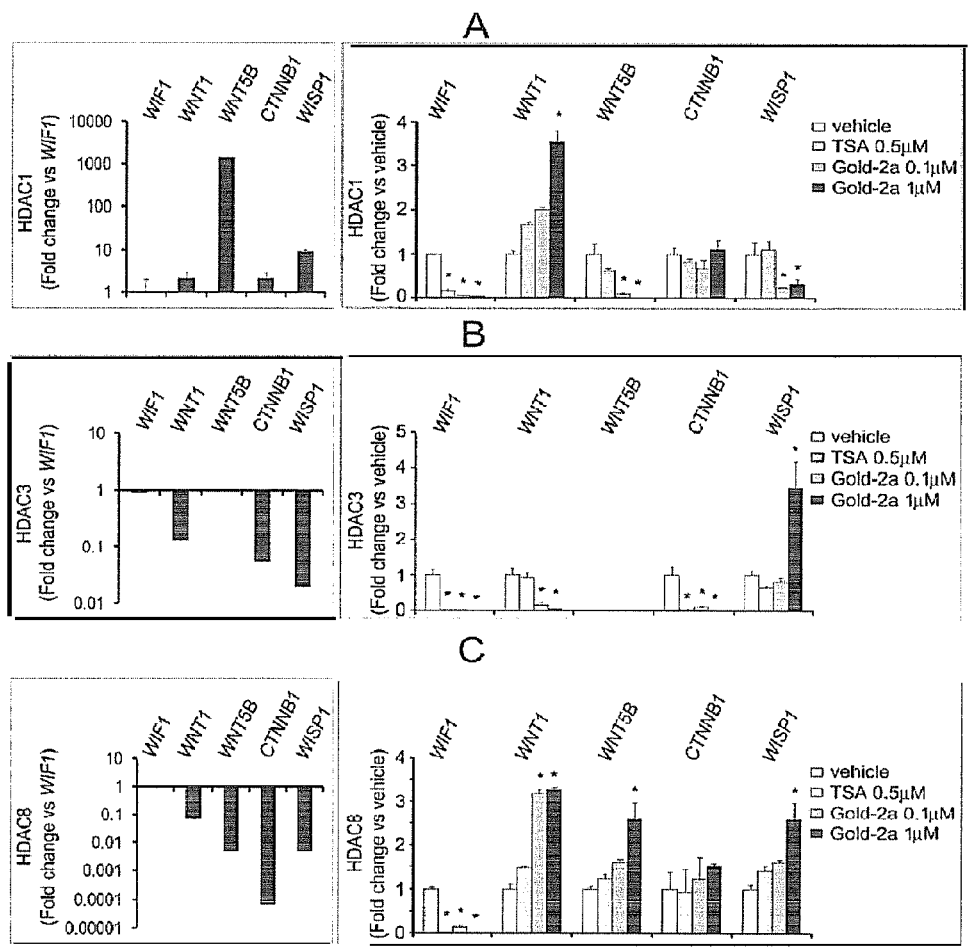
FIG. 7 shows that gold-2a differentially regulates the associations of class I HDACs to the promoter regions of the five Wnt signaling molecules.

Among the four members of class I HDACs, HDAC2 could not be detected at the promoters of all five Wnt pathway genes, despite that it was present at the promoter of ESR1. The abundance of HDAC1, HDAC3 and HDAC8 was highly variable at the promoter regions of these genes (FIG. 7). HDAC1 was more abundantly associated with WNT5B than other promoters. HDAC3 was not associated with WNT5B promoter. The amounts of HDAC3 and HDAC8 at WIF1 promoter were much higher than the other four genes. The highest and lowest association could differ by as much as 10,000 times. With this information, the significant fold increases that were below 10 may not be biologically important. On the other hand, gold-2a, to a greater extent, elicited inhibitory effects on the associations of different HDACs to the promoters of WIF1, WNT1, WNT5B and CTNNB1. In samples treated with 1 μM gold-2a, HDAC1 at the promoters of WIF1 and WNT5B was dramatically decreased by 54 and 164 folds, respectively; HDAC3 at the promoters of WIF1, WNT1 and CTNNB1 was down-regulated by 193, 23 and 162 folds, respectively; the binding of HDAC8 to WIF1 promoter was also found to be down-regulated by about 300 folds.

FIG. 7 shows that gold-2a differentially regulates the associations of class I HDACs to the promoter regions of the five Wnt signaling molecules. ChIP-PCR was performed in MDA-MB-231 cells that had been treated with or without drug compounds at indicated concentrations for 24 hours. The associations of HDAC1 (A), HDAC3 (B) and HDAC8 (C) were quantified by real time PCR analysis as described in Methods. Left panel: The amount of each HDAC bound to the promoter regions of individual gene was compared and calculated as fold change vs WIF1 to reflect their relative abundances. The y-axis was at logarithmic scale. Right panel: The associations of HDAC1, HDAC3 or HDAC8 to the promoters of WIF1, WNT1, WNT5B, CTNNB1 and WISP1 were quantified and calculated against vehicle control samples. *, P<0.01, n=3. Note all increased values were below 10 folds and not considered here.

To understand how gold-2a interacts with class I HDAC, docking studies were performed by using flexible-ligand docking module of ICM-Pro 3.6-1 molecular software (Molsoft, http://www.molsoft.com). Because only HDAC8 X-ray crystal structures are available among class I HDAC, the co-complex crystal structure of HDAC8 with TSA (PDB code: 1T64) (http://www.rcsb.org) was employed for molecular docking. Comparative analysis of the low-energy gold-2a conformations suggested that the preferred site for gold-2a binding was on the surface of the binding pocket of HDAC8 (FIGS. 8C-E) with a strong binding interaction (as reflected by the binding energy of −9.67 kcal/mol). As a reference, molecular docking of known HDAC inhibitor—TSA showed an interaction energy of −10.28 kcal/mol (FIG. 8A), the root mean square deviation (RMSD) is within 1.0 Å when compared with the position of co-complex X-ray crystal structure of TSA (PDB code: 1T64). Moreover, molecular docking of reported HDAC inhibitor cyclic tetrapeptide showed an interaction energy of −7.78 kcal/mol, and the long acyclic chain in tetrapeptide is buried inside the 11 Å channel (FIG. 8B). Unlike the mode of binding of TSA and cyclic tetrapeptide, the side chains of gold-2a would not buried inside the 11 Å channel, and the lowest energy binding pose of gold-2a is characterized by the porphyrin ring motif filling the hydrophobic pocket and being in close contact within 4 Å with amino acid residues Tyr100, Gly151, Phe152, His180, Pro273, Met274 and the OH group of gold-2a pointing towards the 14 Å internal cavity of HDAC8 (FIG. 8E), which in turn, blocking the exit of the 14 Å internal cavity of HDAC8.

Figure 8:
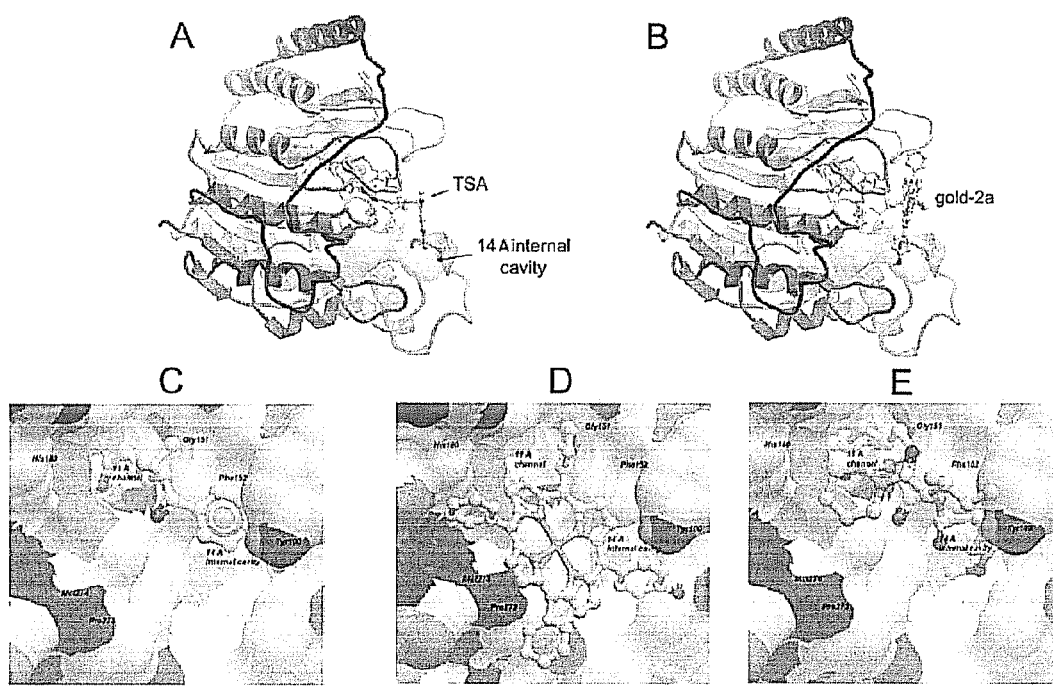
FIG. 8 shows the molecular representations of different HDAC8-HDACi complexes.

FIG. 8 shows the molecular representations of different HDAC8-HDACi complexes. Docking models were shown as the low-energy pose in HDAC8 (ribbon form) for TSA (A) and gold-2a (B). Both drugs were depicted as the stick model.

With respect to any figure or numerical range for a given characteristic, a figure or a parameter from one range may be combined with another figure or a parameter from a different range for the same characteristic to generate a numerical range.

Other than in the operating examples, or where otherwise indicated, all numbers, values and/or expressions referring to quantities of ingredients, reaction conditions, etc., used in the specification and claims are to be understood as modified in all instances by the term "about."

While the invention has been explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A method for treatment of nasopharyngeal carcinoma comprising administering to a patient that has nasopharyngeal carcinoma a composition comprising a therapeutically effective amount of a gold(III) complex having the structural formula of

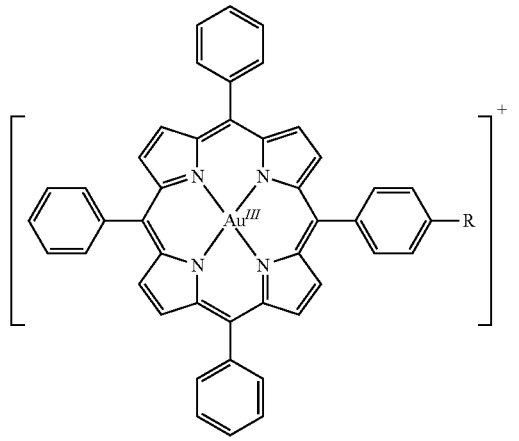

or a pharmaceutically acceptable salt thereof, wherein:
R is selected from the group consisting of —OH; and
X is independently a pharmaceutically acceptable counter-ion.

2. The method according to claim 1, wherein the gold(III) complexes induce apoptosis in cancer cells.

3. The method of claim 1, wherein the gold(III) complex inhibits histone deacetylase activity by binding to histone deacetylase.

4. A method for treatment of breast carcinoma comprising administering to a patient that has breast cancer a composition comprising a therapeutically effective amount of a gold (III) complex having the structural formula of

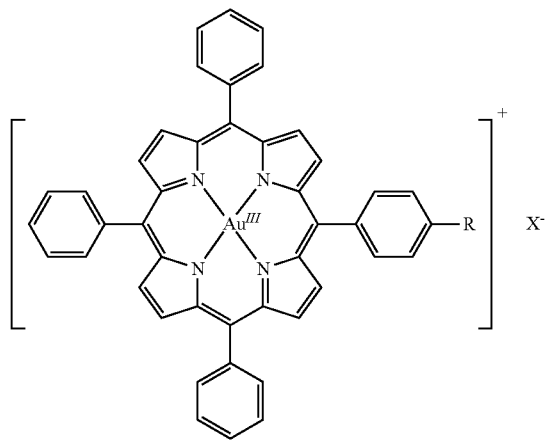

or a pharmaceutically acceptable salt thereof, wherein:
R is selected from the group consisting of —OH; and
X is independently a pharmaceutically acceptable counter-ion.

5. The method of claim 4, wherein the gold(III) complex inhibits histone deacetylase activity by binding to histone deacetylase.

6. The method according to claim 4, wherein the gold(III) complexes induce apoptosis in cancer cells.

7. A method for treatment of liver cancer comprising administering to a patient that has liver cancer a composition comprising a therapeutically effective amount of a gold(III) complex having the structural formula of

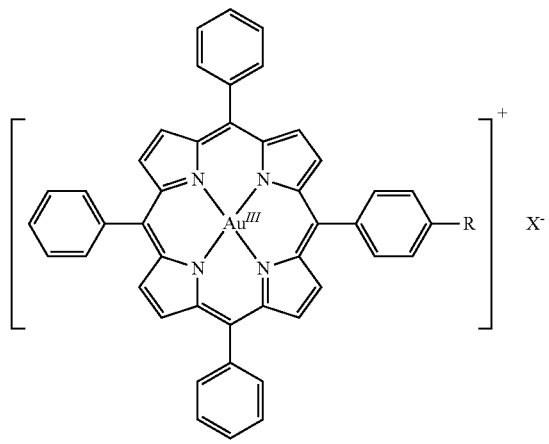

or a pharmaceutically acceptable salt thereof, wherein:
R is selected from the group consisting of —OH; and
X is independently a pharmaceutically acceptable counter-ion.

8. The method of claim 7, wherein the gold(III) complex inhibits histone deacetylase activity by binding to histone deacetylase.

9. The method according to claim 7, wherein the gold(III) complexes induce apoptosis in cancer cells.

* * * * *